(12) United States Patent
Viscomi et al.

(10) Patent No.: US 7,037,109 B1
(45) Date of Patent: May 2, 2006

(54) INTER-PROXIMAL CONTACT DENTAL MATRIX BAND

(76) Inventors: Dominic Anthony Viscomi, 1868 Fecility La., Hellertown, PA (US) 18055; Brian David Viscomi, 500 Central Ave, Union City, NJ (US) 78087

( * ) Notice: Subject to any disclaimer, the term of this patent is extended or adjusted under 35 U.S.C. 154(b) by 1 day.

(21) Appl. No.: 10/651,059

(22) Filed: Aug. 28, 2003

(51) Int. Cl.
*A61C 5/04* (2006.01)

(52) U.S. Cl. .................................................. 433/39
(58) Field of Classification Search ................ 433/39, 433/155
See application file for complete search history.

(56) References Cited

U.S. PATENT DOCUMENTS

| 1,669,231 | A | * | 5/1928 | Curran ........................ 433/39 |
| 2,591,744 | A | | 4/1952 | Tofflemire |
| 2,594,367 | A | * | 4/1952 | Tofflemire ................... 433/39 |
| 3,921,299 | A | * | 11/1975 | Lazarus ....................... 433/39 |
| 4,024,643 | A | | 5/1977 | Eisenberg |
| 5,330,353 | A | | 7/1994 | Waverin |
| 5,788,487 | A | * | 8/1998 | Meyer ......................... 433/39 |

* cited by examiner

*Primary Examiner*—John J Wilson

(57) ABSTRACT

A thin, flexible, gently angled boomerang shaped matrix band (2) having an extrusion window (6) located within the medial portion of the band's (2) inferior and superior borders. Located inferiorly, a gingival separation notch, (10) is medially aligned with and terminates a measured distance below the extrusion window (6). Located superiorly, a semicircular bridge (8) is medially aligned with both the extrusion window (6) and the gingival separation notch (10).

12 Claims, 11 Drawing Sheets

INTER-PROXIMAL CONTACT DENTAL MATRIX BAND

CROSS-REFERENCE TO RELATED APPLICATION

NONE

FEDERALLY SPONSORED RESEARCH

Not Applicable

SEQUENCE LISTING OR PROGRAM

Not Applicable

BACKGROUND OF THE INVENTION—FIELD OF INVENTION

This invention relates to the field of dentistry, specifically an improved matrix band having an aperture, gingival separation notch, and a connecting bridge for band support, separation and aperture placement

BACKGROUND OF THE INVENTION

Complex cavity preparations of posterior teeth require a supporting or retaining wall to contain the restorative materials within the confines of the tooth till such time that the filling material achieves a setting or hardening state. Previous retaining systems were conceived to deal with the traditional metal-based, or amalgam filling materials.

They availed of amalgam's physical properties of multi-directional expansion through its hardening phase. Therefore, retaining mediums separating the inter-proximal areas between a prepared tooth and its abutting neighbor could be successfully removed while ensuring that positive tooth to filling contact would ensue.

The matrix band U.S. Pat. No. 2,591,744 to Tofflemire, T. F. 1952, the industry standard and staple matrix band, served the profession well. It encircled the tooth and provided a rigid wall with which to contain the amalgam restorative material. Although a separating wall remained until the filling material reached its hardening phase, amalgam's expansion capabilities plus moderate inter-proximal wedging tooth separation maintained the desired restoration to tooth contact upon removal of the barrier wall. Thus, potential inter-proximal food impaction and subsequent gingival or gum irritation were eliminated. We shall, however, demonstrate the band's short-comings with alternative and current restorative materials.

The advent of tooth colored restorative materials, namely composite resins, is in response to amalgam's questionable toxicity due to its mercury component, and the demand for esthetics. However, one of the major inadequacies of composite resin materials is the antithesis of amalgam's forte, that is, it contracts rather than expand while hardening, or polymerizing. Conventional matrix retaining systems therefore allowed for an inter-proximal gap to remain upon removal of the matrix separating wall. This exposed the inter-proximal area to the aforementioned pathology, that is food impaction and gum irritation. Prior arts' remedy for this introduced a thinner metal matrix material to reduce the thickness of the separating wall, and non-metal or mylar strips, in conjunction with enhanced wedging or separation between the teeth. This potentially allows for more filling material to be introduced into the cavity preparation to compensate for anticipated shrinkage. These attempts proved to be not without limitations. Mylar strips lack sufficient rigidity, and their placement presented ergonomic challenges. The introduction of thinner metal matrices still required a barrier wall to remain during the setting phase, and thus did not ensure a consistent desired inter-proximal contact. These present as a major disadvantage to a technique sensitive restorable material. In addition, present day composite resins have dual cure capabilities, that is the application of the curing light medium allows the resin to self-cure or harden and lessens its dependency on the light. This feature obviates the need for transparent retaining barriers and allows the dentist to use standard matrix retaining apparatuses.

U.S. Pat. No. 5,330,353 to Wavrin, Dennis L. 1994, presents a band with a plastic, or celluloid based inter-proximal contact area, attached between adjacent metal lateral extensions. Plastic's inherent lack of rigidity complicates the band's insertion, and allows for the unavoidable escape of filling material into unwanted areas. In addition, composite resin's dual curing properties eliminates the need for transparency in a matrix system. The Wavrin band can also contraindicate the employment of a rubber dam or isolation barrier essential for successful placement of current moisture sensitive composite resins. Furthermore, the band's retaining wall that is present at the completion of the filling's condensation and polymerization can, upon removal, result in an undesirable gap, or open contact. In addition, the band's fabrication requirements of micro-etching and epoxy adhesives to conjoin the segments can add considerably to the production costs of an essentially disposable, single use device.

U.S. Pat. No. 4,024,643 to Eisenberg, Harry H. 1977, presents a longitudinally split dental matrix band with a windowed opening at the contact area. This embodiment allows for extrusion of the compacted composite resin to abut directly to the adjacent tooth. However, the band's window, which is disjoined on one side, can contribute to unpredictable filling overflow, with subsequent contour and finishing challenges. This contraindicates multi-surface tooth restorations. Also, the window configuration of the band presents engagement with the polymerized resin to the extent that band removal may lacerate fragile gingival tissue thus contaminating the field of operation and contributing to unnecessary post-operative patient discomfort. Furthermore, the band's tension producing concept possesses ergonomic drawbacks presenting the clinician with insertion challenges in the posterior regions of the oral cavity. Engagement of this tension apparatus may also conflict with usage of the required rubber dam isolation.

BACKGROUND OF INVENTION OBJECTS AND ADVANTAGES

Accordingly, several objects and advantages of the present patent application of Dominic A. Viscomi and Brian D. Viscomi for Inter-Proximal Contact Matrix Band are:

(a) Band features allow a predictable, positive and desirable contact between the adjacent teeth and composite resin.

(b) Band configuration permits for simultaneous multiple tooth surface restoration.

(c) Band is compatible with rubber dam isolation and moisture control barrier devices.

(d) Removal system ensures that the polymerized composite extrusion will not sustain damage.

(e) Band removal is a-traumatic to sensitive gingival tissue.
(f) Dual-purpose design allows for usage of both composite and amalgam restorative materials.
(g) Implementation of traditional band design does not require the use of specialized instruments or retainers.
(h) Predictable restoration to tooth inter-proximal contact allows for increased operator productivity.

Further objects and advantages are for the band to be readily incorporated into standard operative techniques while being compatible with existing chair-side armamentarium. The band eliminates the need for multiple matrix retaining systems thus providing economies of purchase. Still further objects and advantages will become apparent from a consideration of the ensuing description and drawings.

SUMMARY OF THE INVENTION

The invention is a modified boomerang-shaped, semi-flexible dental matrix band for enveloping around a first tooth having been prepared for a cavity (preparation not shown) and the first tooth having a contact point with a second tooth. The band exhibits an opening, or window adjacent to the contact point of the second tooth. This allows for the extrusion of compacted filling material in the prepared tooth to directly touch the second tooth's contact point permitting exposure to a curing light medium and subsequent resin polymerization. Located above the window opening, a semicircular extension of metal, in medial alignment with the window is used as a guide to locate the window properly with the contact point of the adjacent tooth. It also serves as an initiation point for band separation. Below the semicircular appendage and window is a medially located separation notch that is used to further facilitate the band's separation and removal.

DRAWINGS

Figure 13:
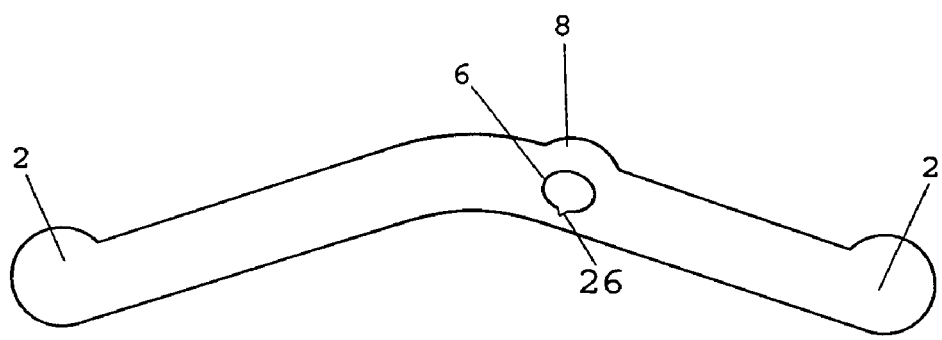
Figure 14:
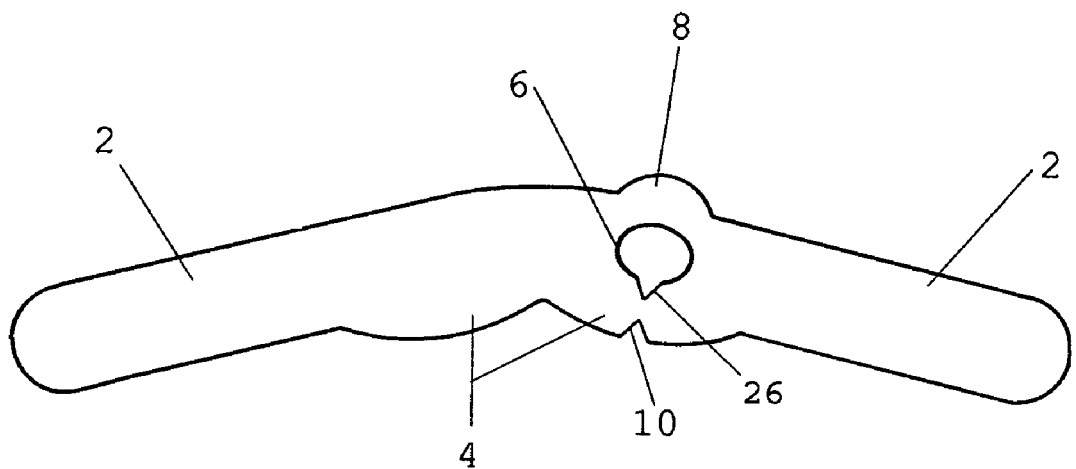
Figure 15:
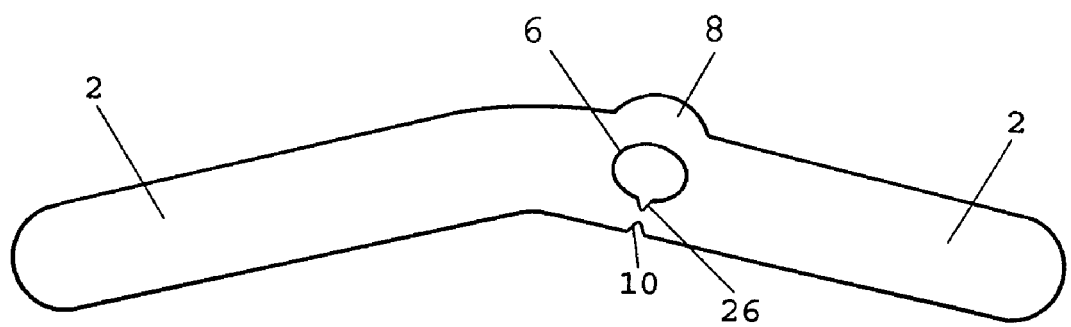

FIG. 13 shows a deciduous tooth matrix band with an inferior window separation notch contiguous with the inferior border of the extrusion window FIG. 14 shows an embodiment with extrusion window, gingival separation notch and inferior window separation notch FIG. 15 shows an embodiment with extrusion window, gingival separation notch, inferior window separation notch and no inter-proximal gum extensions.

Figure 16:
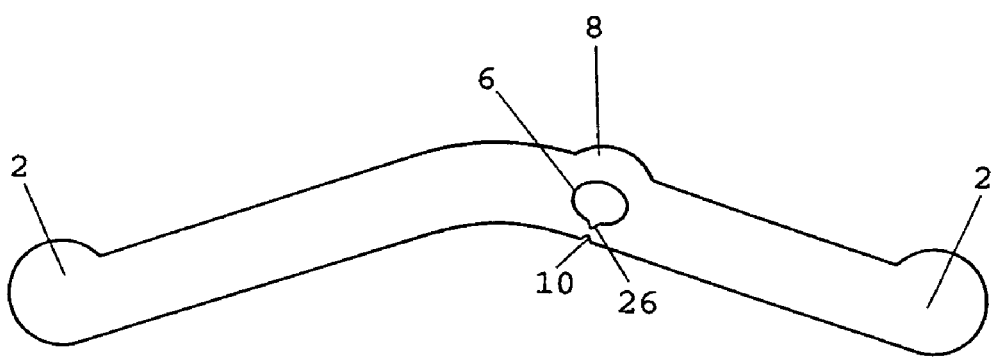
Figure 17:
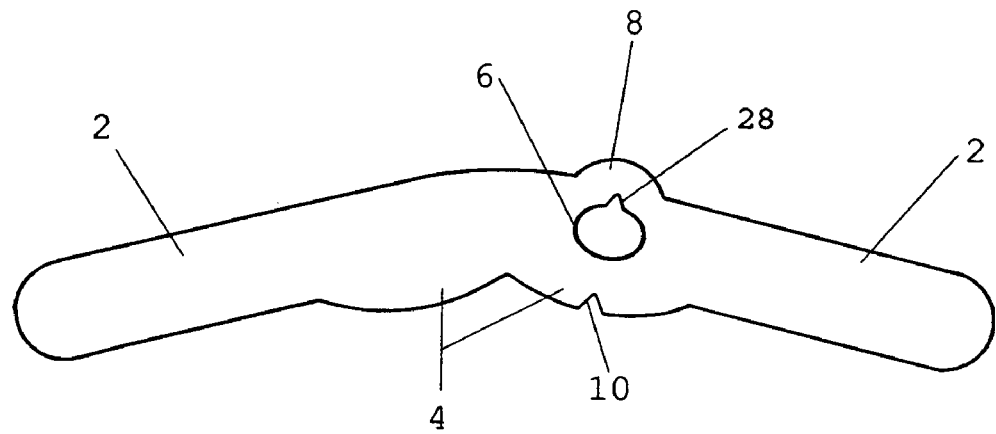

FIG. 16 shows a deciduous tooth matrix band embodiment with extrusion window, gingival separation notch, and inferior window separation notch FIG. 17 shows a matrix band with a gingival separation notch, and superior window separation notch.

Figure 18:
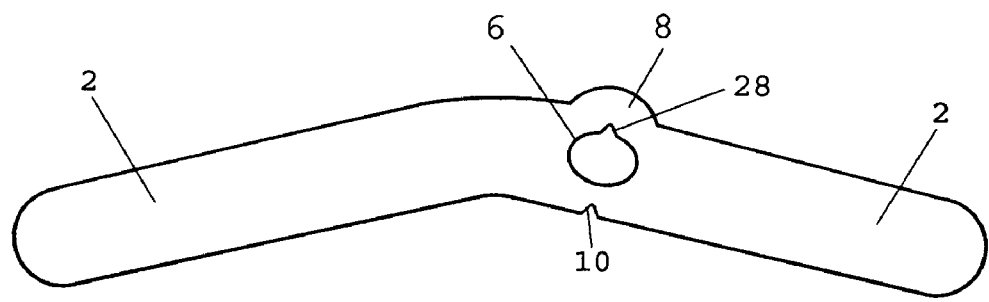

FIG. 18 shows a matrix band with, with a gingival separation notch, superior window separation notch and no inter-proximal gum extensions.

Figure 19:
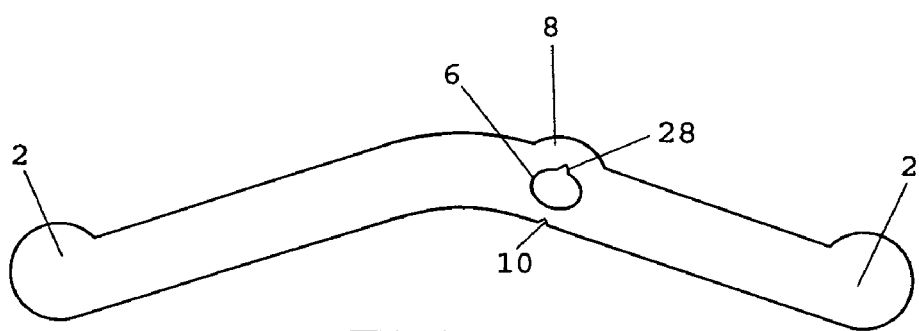

FIG. 19 shows a deciduous tooth matrix band with a gingival separation notch, and superior window separation notch.

Figure 20:
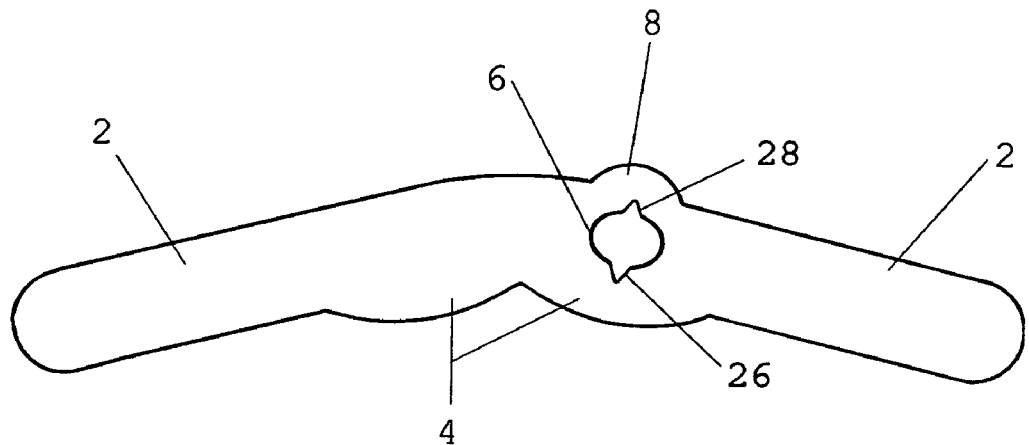

FIG. 20 shows an embodiment with an inferior window separation notch and superior window separation notch.

Figure 21:
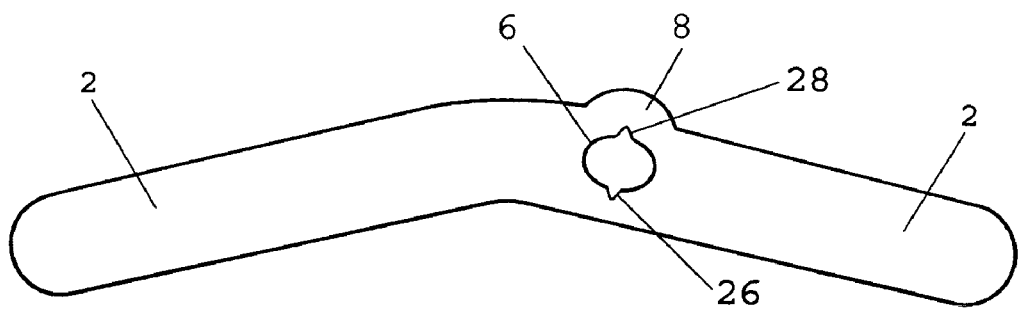

FIG. 21 shows an embodiment with an inferior window separation notch, superior window separation notch and no gum extensions.

Figure 22:
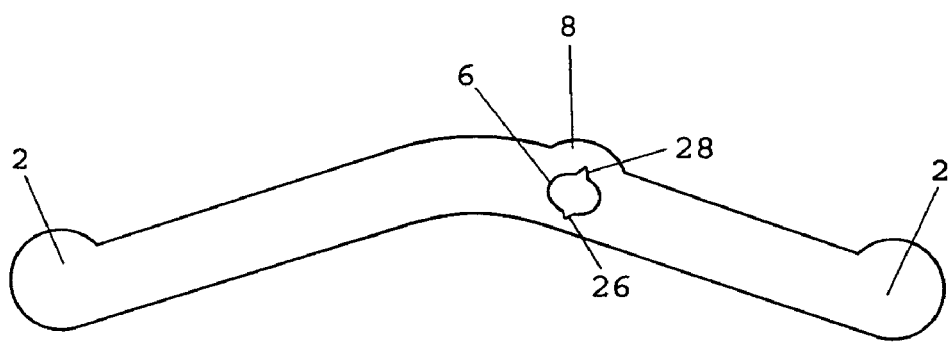
Figure 23:
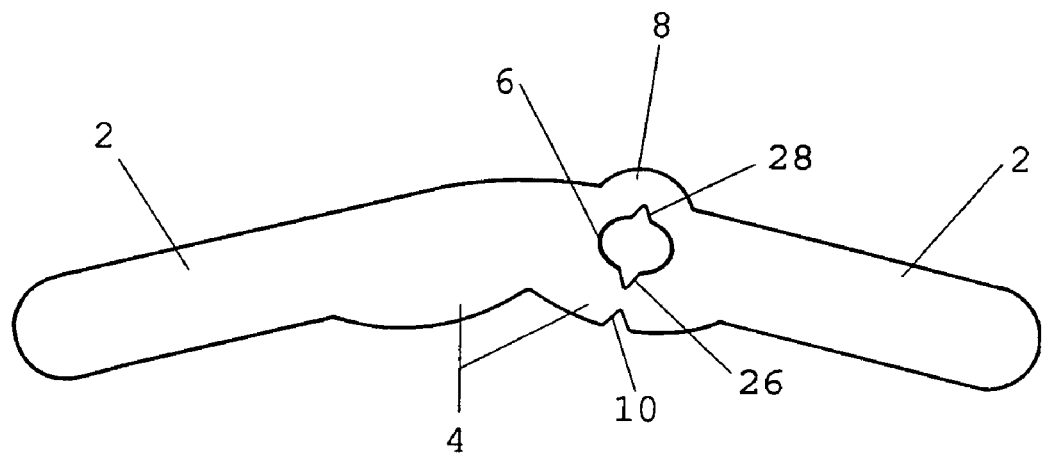

FIG. 22 shows a deciduous tooth matrix band embodiment with an inferior window separation notch and a superior window separation notch FIG. 23 shows a matrix band embodiment with gingival separation notch, inferior window separation notch and superior window separation notch.

Figure 24:
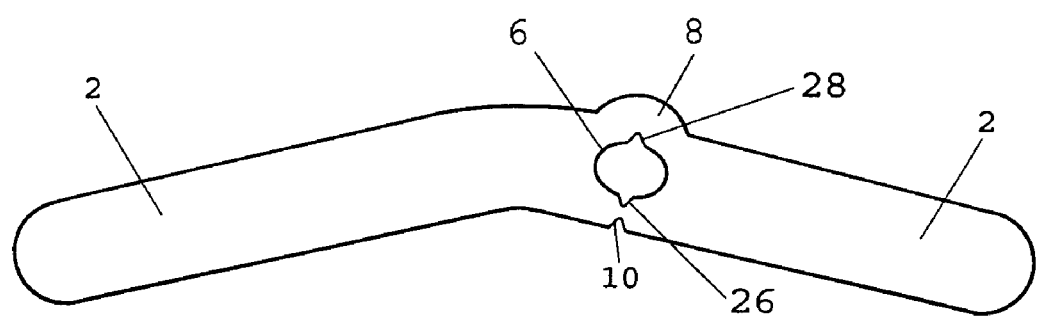

FIG. 24 shows an embodiment with embodiment with gingival separation notch, inferior window separation notch, superior window separation notch and no gum extensions.

Figure 25:
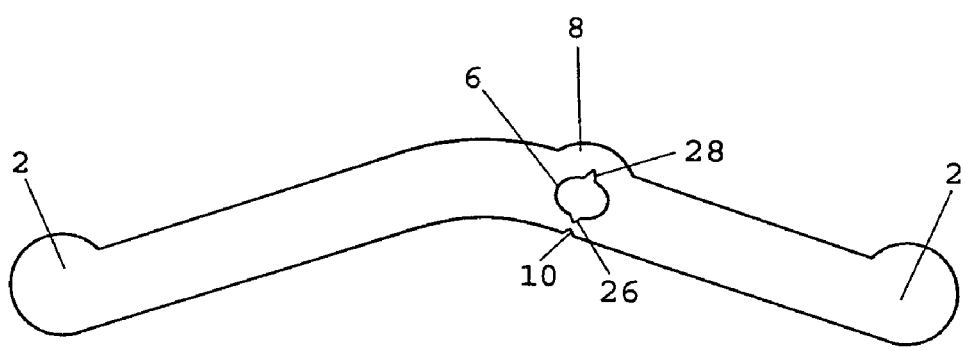

FIG. 25 shows deciduous tooth matrix band embodiment with a gingival separation notch, inferior window separation notch and superior window separation notch.

| DRAWINGS - LIST OF REFERENCE NUMERALS | | | |
|---|---|---|---|
| 2 | matrix band | 4 | inter-proximal gum extension |
| 6 | extrusion window | 8 | bridge |
| 10 | gingival separation notch | 12 | retainer |
| 14 | first molar | 16 | composite filling |
| 18 | composite filling extrusion | 20 | condensing instrument |
| 22 | scissor | 24 | second molar |
| 26 | inferior window notch | 28 | superior window notch |

DETAILED DESCRIPTION—FIG. 1
PREFERRED EMBODIMENT

Figure 1:
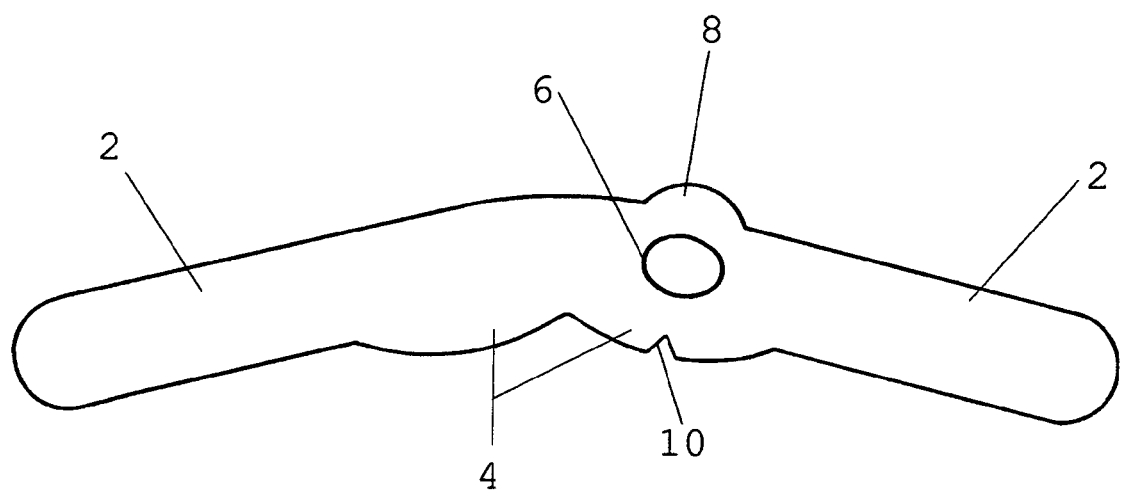
FIG. 1 shows a frontal view of the inter-proximal contact composite matrix band in a preferred embodiment.
Figure 2:
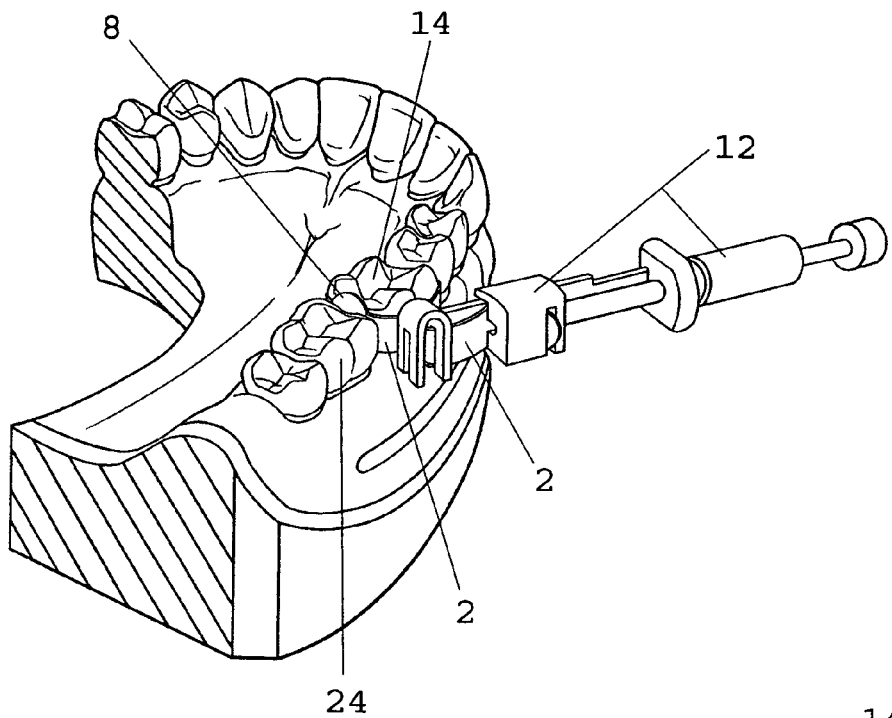
FIG. 2 shows an overview of the matrix band and retainer attached to the maxillary first molar.
Figure 3:
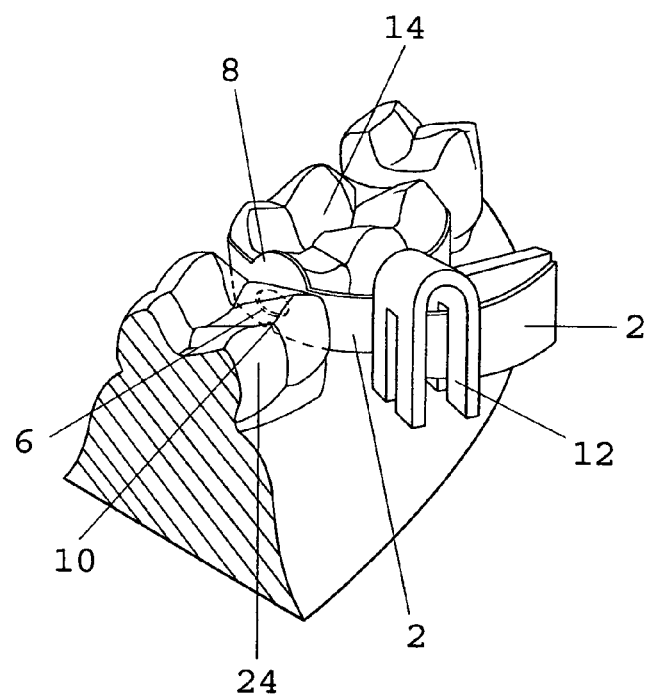
FIG. 3 shows the matrix band's features visible through the mesial surface of the maxillary second molar, indicated by the dotted lines.
Figure 4:
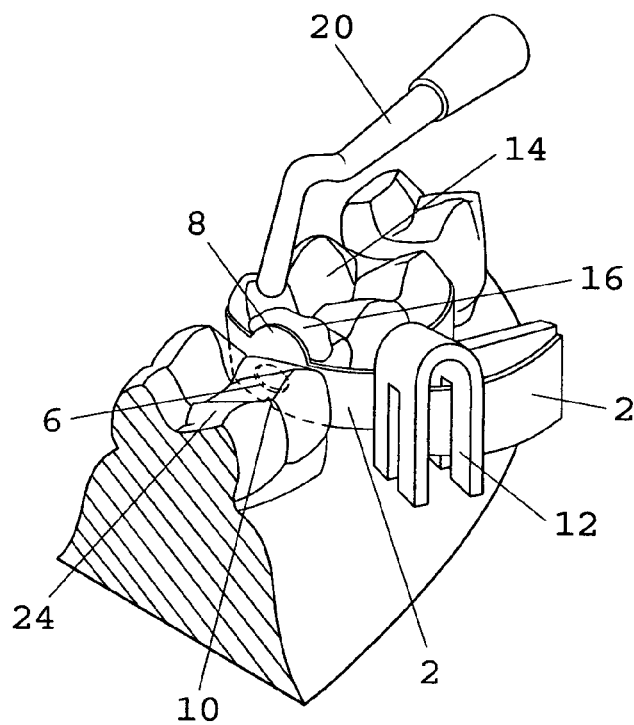
FIG. 4 shows the composite resin filling applied to a prepped tooth with a condensing instrument pictured above.
Figure 5:
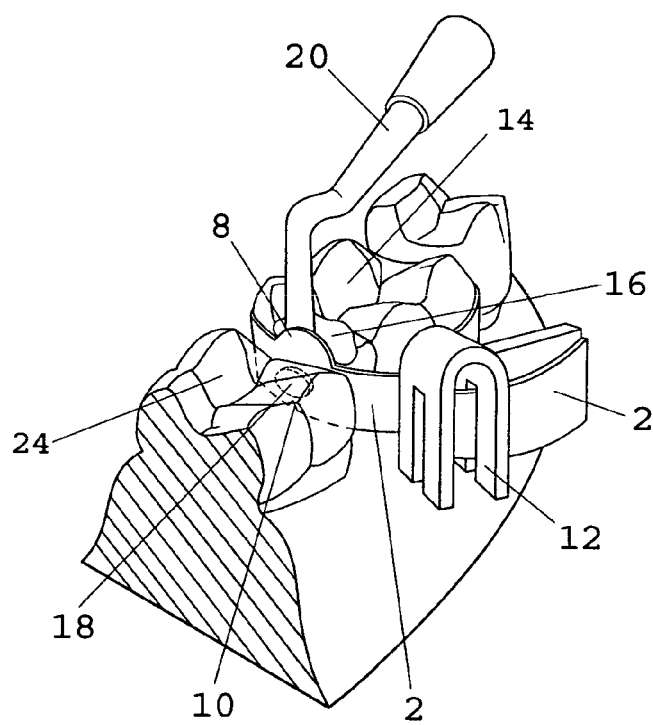
FIG. 5 shows condensing of the composite resin material by the filling instrument with resultant extrusion through the band's window.

A preferred embodiment of the present invention is illustrated in FIG. 1 (front view). The Inter-Proximal Contact Matrix Band 2 is a mildly angled flexible band with a distinct boomerang shape that is wrapped around a tooth and fastened by a retainer instrument 12 (FIG. 2). The matrix band 2 is preferably fabricated from a biocompatible metal such as stainless steel, plastic, or other semi-rigid material machine pressed or stamped into the proper configuration. Originating from the inferior medial region of the matrix band 2 are two semi-circular protrusions, bulges, or inter-proximal gum extensions 4. Located above one of the extensions 4, within the matrix band's 2 interior, generally located off the band's 2 center point is a hole, aperture or extrusion window 6. The window 6 is generally ovoid and is of a size and dimension as to rest within the inter-proximal space between the contact areas of the first 14 and second molars 24 (FIG. 3). The window 6 as is with the band 2, is machine pressed or stamped into proper configuration. Interrupting one of the inter-proximal gum extensions 4, and in medial alignment with, and inferior to the extrusion window 6 is a gingival separation notch 10. Superior to the extrusion window 6 is a semi-circular expanse of uninterrupted metal called the bridge 8. The location of the bridge 8 resides directly above both the extrusion window 6 and the gingival notch 10 on the matrix band's 2 superior border. Both the bridge 8 and gingival notch 10 are fashioned by machine pressing or stamping.

ALTERNATIVE EMBODIMENTS—FIGS. 9–25

Figure 9:
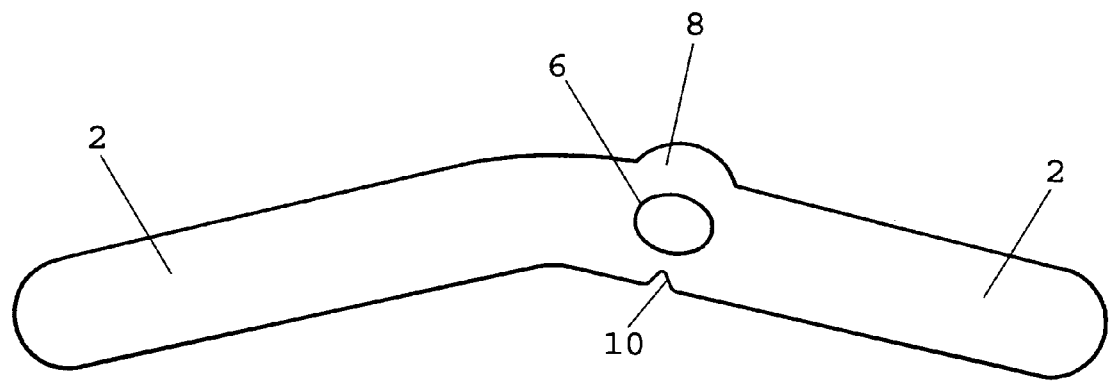
FIG. 9 shows a front view of an alternative embodiment with extrusion window, gingival separation notch, semi-circular bridge, and no inter-proximal gum extensions.
Figure 10:
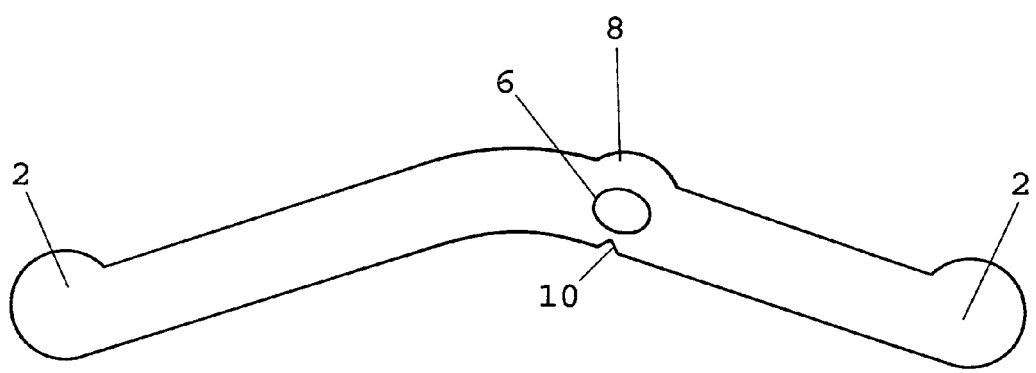
FIG. 10 shows a deciduous or small tooth matrix band with extrusion window, gingival separation notch and semi-circular bridge.
Figure 11:
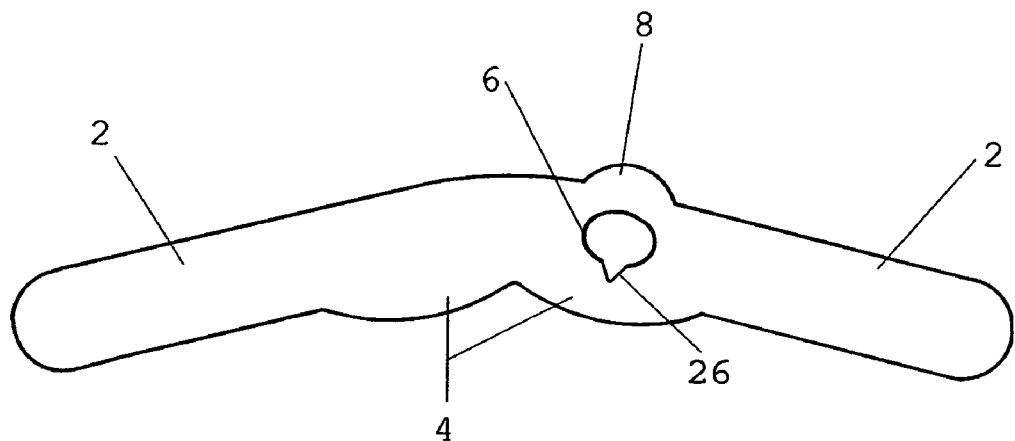
FIG. 11 shows an embodiment with an inferior window separation notch contiguous with the inferior border of the extrusion window.
Figure 12:
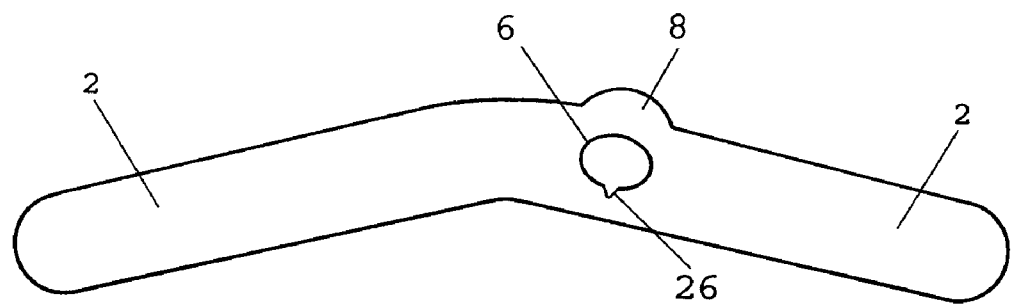
FIG. 12 shows an embodiment with an inferior window separation notch contiguous with the inferior border of the extrusion window and no inter-proximal gum extensions.

There exist various possibilities with regard to the Inter-Proximal Contact Matrix Band 2 shape. For example, FIG. 9 portrays a matrix band 2 with an extrusion window 6, bridge 8, and gingival separation notch 10. Eliminated in this embodiment is the presence of inter-proximal gum extensions 4. In FIG. 10 the extrusion window 6, bridge 8 and gingival separation notch 10 features are embodied on a matrix band 2 intended for deciduous or small teeth. FIG. 11 shows a band with extrusion window 6, bridge 8, inferior window separation notch 26 and inter-proximal gum extensions 4. FIG. 12 presents an embodiment with extrusion window 6, bridge 8 and inferior window separation notch 26. Omitted in this embodiment is the presence of inter-proximal gum extensions 4. FIG. 13 presents a deciduous or small tooth band embodiment with extrusion window 6, bridge, 8 and inferior window separation notch 26. FIG. 14 depicts an embodiment with gum extensions 4, extrusion window 6 gingival separation notch 10 and inferior window separation notch 26. FIG. 15 presents an embodiment with an extrusion window 6 and gingival separation notch 10 and inferior window separation notch 26. Absent in this embodiment is the presence of gum extensions 4. FIG. 16 presents a deciduous or small tooth embodiment with an extrusion window 6, bridge 8, gingival separation notch 10 and inferior window separation notch 26. FIG. 17 is an embodiment with gum extension 4, extrusion window 6, gingival separation notch 10 and superior window separation notch 28. FIG. 18 is an embodiment with extrusion window 6, bridge 8, gingival separation notch 10 and superior window separation notch 28. Both gum extensions 4 are omitted in this embodiment. FIG. 19 is a deciduous tooth band embodiment featuring extrusion window 6, bridge 8, gingival separation notch 10, and superior window separation notch 28. FIG. 20 is an embodiment with extrusion window 6, bridge 8, inferior window separation notch 26 and superior window separation notch 28. FIG. 21 shows an embodiment with extrusion window 6, bridge 8, inferior window separation notch 26 and superior window separation notch 28. The gum extensions 4 are omitted.

FIG. 22 presents a deciduous band embodiment with extrusion window 6, bridge 8, inferior window separation notch 26 and superior window separation notch 28. FIG. 23 is an embodiment with extrusion window 6, bridge 8, gingival separation notch 10, inferior window separation notch 26 and superior window separation notch 28. FIG. 24 is a band embodiment with extrusion window 6, bridge 8, gingival separation notch 10, inferior window separation notch 26 and superior window separation notch 28. The gum extensions 4 are omitted. FIG. 25 shows a deciduous band embodiment with extrusion window 6, bridge 8, gingival separation notch 10, inferior window separation notch 26 and superior window separation notch 28.

Operation FIGS. 2–8

Figure 6:
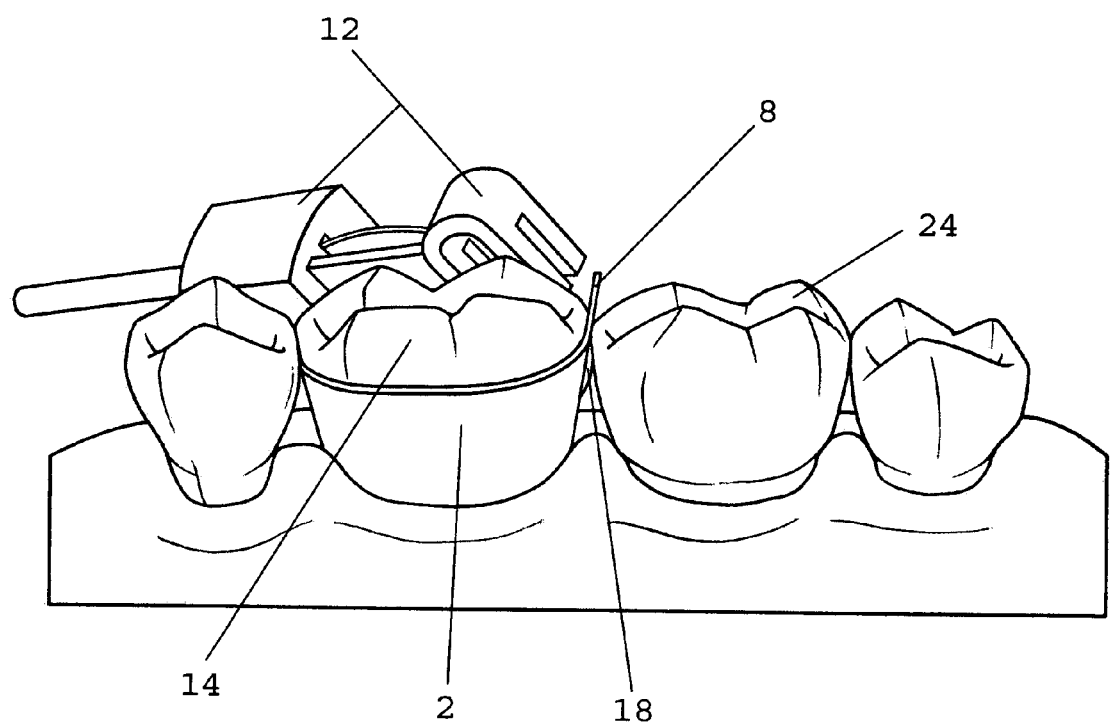
FIG. 6 shows the composite extrusion's inter-proximal contact between the first and second molars from an inner-mouth view.
Figure 7:
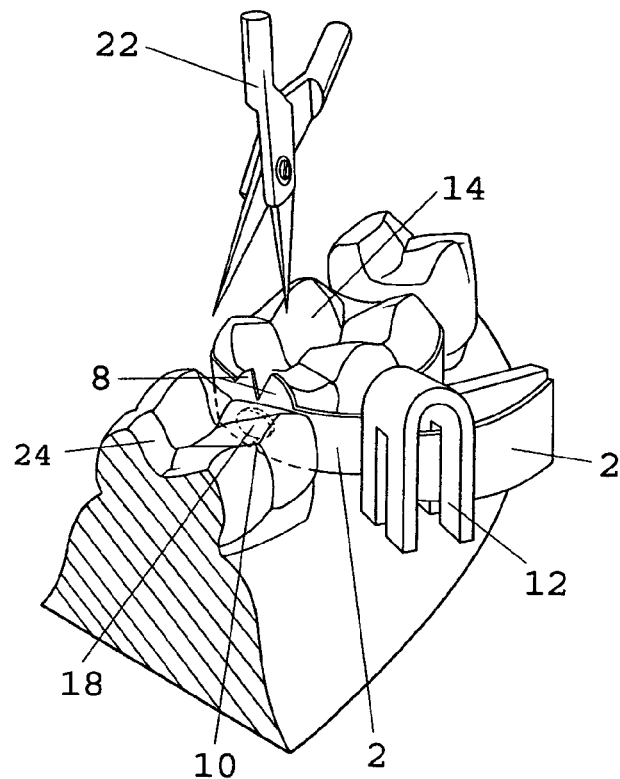
FIG. 7 shows the initiation of the matrix band separation with a scissor snipping the connecting bridge.
Figure 8:
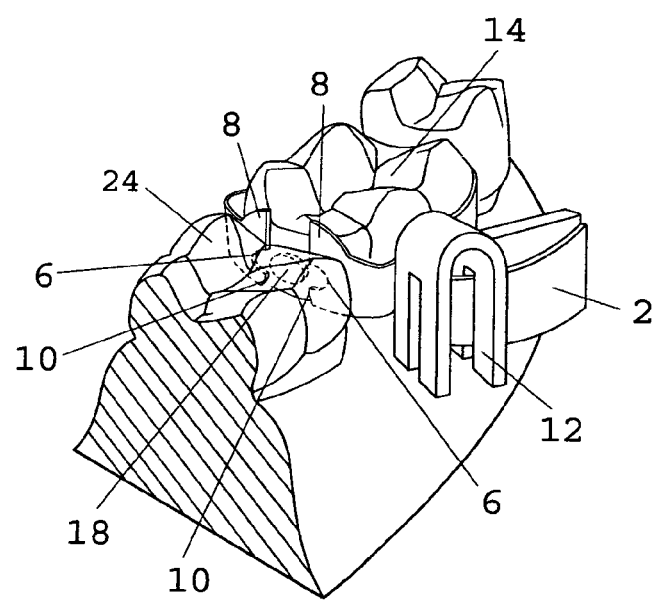
FIG. 8 shows the termination of the matrix band removal process upon band tightening.

Following tooth preparation (not shown), a rubber dam or moisture barrier is placed to isolate the tooth and to procure a dry working field (not shown). In FIG. 2, an overview of the maxillary dental arch is displayed with an Inter-proximal Contact Dental Matrix Band 2 and retainer 12 engaging the first molar 14. The band 2 is affixed to a conventional Tofflemire retainer 12, which is well known in the art. The operation of such retainer 12 is also well known in the art, as its use is the mainstay of traditional restorative dentistry. In FIG. 2, the retainer 12 is positioned to allow the matrix band 2 to be placed securely around the circumference of the first molar 14. Once secured in place, the extrusion window 6 portion of the band 2 is positioned in the inter-proximal space between the first molar 14 and second molar 24, as seen in FIG. 3. Positioning of the window 6 should be centered where tooth contact occurs between the first molar 14 and second molar 24. To this end, the band's bridge 8 is used as a centering device, since it is direct alignment with the extrusion window 6. Once desired alignment is achieved, the bridge 8 extends inter-proximally above the molars. A separating wedge (not shown) is placed to secure the gingival inferior portion of the band 2 against the side of the first molar 14. Next, in FIG. 4, an appropriate amount of composite resin material 16 is placed within the prepared cavity of the first molar 14. With a condensing instrument 20, the composite filling material 16 is spread within the prepared surface of the first molar 14. Through applied pressure of the condensing instrument 20 in FIG. 4, composite filling 16 material is forced into the void created by the first molar's 14 cavity preparation and the Inter-Proximal Contact Matrix Band 2. Through subsequent condensing, composite filling material 16 then extends through the extrusion window 6. The result is a composite filling extrusion 18 that creates direct contact inter-proximally with the second molar 24. FIG. 6 shows a lateral view of the filling extrusion 18 passing through the extrusion window 6, and making contact with the second molar 24. Upon polymerization from an externally applied light source, (not shown), the band 2 is removed in two steps. In FIG. 7, a scissor 22 is used to snip the bridge 8 to the top edge of the first molar 14, thus initiating the first stage of separation. Next, in FIG. 8, the retainer 12 is tightened (not shown) until the gingival separation notch 10 yields and separates, allowing for safe, convenient removal from the filling extrusion 18 and first molar 14. Because the conventional Tofflemire retainer 12 is the mainstay of the restorative Dentist's armamentarium, and present day composite resins possess dual curing qualities, the Inter-Proximal Contact Dental Matrix Band 2 is the appropriate choice for posterior composite restorations.

Advantages

From the description above, a number of advantages of my Composite Contact Dental Matrix Band become evident.
  (a) Use of band employs traditional techniques and armamentarium.
  (b) Band's configuration presents for apparent utilization.
  (c) Band's metal consistency permits distortion free insertion and stability during operative procedure.
  (d) Can be used with or without moisture barriers.
  (e) Band's secure relationship to retainer eliminates potential for patient aspiration.

(f) Return visits are minimized due to band's reliability for positive contact.
(g) Conventional retainer serves also as band remover, eliminating need for additional instrumentation.
(h) Band is compatible with dual-cured and self-cured composite resins.

CONCLUSION, RAMIFICATIONS, AND SCOPE

Accordingly, the reader will see that the Inter-Proximal Contact Matrix Band promotes clean, predictable inter-proximal tooth contact. This is possible by the band's ability to allow direct contact of the polymerizing composite resin with the adjacent tooth, while permitting the subsequent band removal in an operator-friendly fashion. This directly translates into a superior result that promotes efficiency while helping to lessen patient discomfort. Furthermore, the Inter-Proximal Composite Contact Matrix band Allows for greater daily productivity by attaining a successful first result.
Presents cost effective fabrication by utilizing traditional band design.
Dual use band design accommodates both composite resin and amalgam filling procedures.
Eliminates frustration associated with inadequate composite filling to tooth contact.
Is compatible with moisture control barriers.
Allows for convenient, a-traumatic removal.
Is compatible with existing chair side armamentarium.
Is operator friendly and economical to use.

Although the above description contains many specifications, these should not be construed as limiting the scope of the invention but merely provides presently preferred embodiments of this invention. For example, component dimensions may be altered, as need dictates. Band shape and width can vary as future needs and procedures demand. The window's shape, size and dimensions may be altered for optimal contact. The window can be circular or elliptical and include any degree of ellipse necessary. Geometric window apertures may also be employed. The bridge feature is alterable to any height dimension or shape, and can be eliminated as need determines. For example, a single or series of notched extrusion window guides may be scored into the bridge's apex to facilitate aligning of the band's extrusion window. Also, the gingival separation notch may be variably angled to complement the contour of the band. the gingival notch may also embody any shape, height and angle as determined for optimal separation. Similar gingival separation notches may be incorporated within the extrusion window itself in order to facilitate band removal. The number location, configuration, and orientation of such notches are also alterable as best suits removal. Lastly, any biocompatible metal, synthetic or other material sufficiently rigid and thin may be used to manufacture the Inter-Proximal Contact Dental Matrix Band.

Thus, the scope of the invention should be determined by the appended claims and their legal equivalents, rather than by the example given.

We claim:

1. A dental matrix band for restoring a tooth with restorative material comprising, a boomerang shaped body having at least one hole, said at least one hole having a periphery contained entirely within said body and said at least one hole having a size and shape for allowing the restorative material to extrude through said at least one hole during use, a contiguous appendage extending above the border of said body and located directly above said at least one hole, said body further comprising at least one weakening notch being contiguous with said hole and extending from the periphery of said at least one hole into the body of the band, whereby, after applying a constrictive force, said at least one hole and said at least one weakening notch allows the band to be easily separated and removed after use.

2. The dental matrix band of claim 1 which possess more than one extrusion window or hole to allow for extrusion of a restorative material.

3. The dental matrix band of claim 1 and further includes a plurality of weakening or separating notches in different configurations to effect a lateral separation through said hole of said band.

4. The dental matrix band of claim 1 wherein said band includes a plurality of weakening or separating notches, and one of said notches is located on the inferior border of said band's body in alignment with said hole.

5. The matrix band of claim 1 wherein said band includes a plurality of weakening or separating notches, and one of the notches is located at the inferior border of said hole.

6. The dental matrix band of claim 1 wherein said band includes a plurality of weakening and separating notches, one of said notches is located on the inferior border of said hole and is in alignment with a second weakening or separating notch which is located on the inferior border of said band's body.

7. The matrix band of claim 1 where said band includes a plurality of weakening or separating notches, and one of the notches is located in the superior aspect of said hole.

8. The matrix band of claim 1 wherein said band includes a plurality of weakening and separating notches, one of said notches is located in the superior aspect of said hole and is in alignment with a second weakening or separating notch which is located on the inferior border of said body.

9. The matrix band of claim 1 wherein said band includes a plurality of weakening and separating notches, one of said notches is located on the inferior border of said hole and is in alignment with a second weakening or separating notch which is located on the superior aspect of said hole.

10. The matrix band of claim 1 wherein said band includes a plurality of weakening and separating notches, one of said notches is located on the inferior border of said body, a second weakening or separating notch is located on the inferior border of said hole or extrusion window, and a third weakening or separating notch located on the superior border of the hole or extrusion window, all of said notches are in alignment with each other.

11. A method for restoring inter-proximal tooth contact comprising:
   (a) providing a boomerang shaped body having at least one hole, said at least one hole having a periphery contained entirely within the body and said hole having a size and shape for allowing the restorative material to extrude through said hole during use, a contiguous appendage extending above the border of said body and located directly above said hole, said body further comprising at least one weakening notch being contiguous with said hole and extending from the periphery of said at least one hole into the body of the band,
   (b) providing a prepared decayed tooth with one or more prepared inter-proximal surfaces,
   (c) attaching said boomerang shaped body to a retaining device and placing said body circumferentially around said decayed prepared tooth aligning at least one said hole with one or more prepared inter-proximal surfaces of a decayed prepared tooth, (d) positioning said at least one said hole with said one or more inter-proximal surfaces,
(e) introducing of a restorative material within the confines of said enveloped prepared tooth such that it will traverse said inter-proximally positioned hole,
(f) administering a number of restorative steps to produce a restored tooth,
(g) removing said boomerang shaped body from said restored tooth.

12. A method for removing a matrix band placed circumferentially around a tooth comprising:
(a) providing a boomerang shaped body having at least one hole, said at least one hole having a periphery contained entirely within the body and said hole having a size and shape for allowing the restorative material to extrude through said hole during use, a contiguous appendage extending above the border of said body and located directly above said hole, said body further comprising at least one weakening notch being contiguous with said hole and extending from the periphery of said at least one hole into the body of the band,
(b) attaching said body to a retaining device and placing said body circumferentially around a tooth with one or more prepared inter-proximal surfaces,
(c) initiating a separation of the superior aspect of said semi-circular appendage,
(d) providing a constrictive force to effect a lateral separation of said boomerang shaped body through said at least one hole,
(e) removing said separated boomerang shaped body from said restored tooth.

* * * * *

UNITED STATES PATENT AND TRADEMARK OFFICE
CERTIFICATE OF CORRECTION

PATENT NO. : 7,037,109 B1
APPLICATION NO. : 10/651059
DATED : May 2, 2006
INVENTOR(S) : Dominic Anthony Viscomi and Brian David Viscomi It is certified that error appears in the above-identified patent and that said Letters Patent is hereby corrected as shown below:

On the Title Page:
(76) Inventors: Dominic Anthony Viscomi, 1868 Fecility La.

Fecility is a mis-print…..should be FELICITY.

Hence: Dominic A. Viscomi, 1868 Felicity La.

Signed and Sealed this

Twenty-second Day of August, 2006

JON W. DUDAS
*Director of the United States Patent and Trademark Office*